United States Patent [19]
Pascaloff

[11] Patent Number: 5,112,299
[45] Date of Patent: May 12, 1992

[54] ARTHROSCOPIC SURGICAL APPARATUS AND METHOD

[75] Inventor: John Pascaloff, Goleta, Calif.

[73] Assignee: Hall Surgical Division of Zimmer, Inc., Carpinteria, Calif.

[21] Appl. No.: 715,304

[22] Filed: Jun. 5, 1991

Related U.S. Application Data

[63] Continuation of Ser. No. 427,438, Oct. 25, 1989, abandoned.

[51] Int. Cl.$^5$ .............................................. A61B 17/32
[52] U.S. Cl. ...................................... 604/22; 606/170; 606/180
[58] Field of Search .................. 606/170, 171, 180; 128/751, 752, 755, 753; 604/22; 30/29.5, 240, 263, 264, 265

[56] References Cited

U.S. PATENT DOCUMENTS

| | | | |
|---|---|---|---|
| 3,384,085 | 6/1968 | Hall | 606/180 |
| 3,882,872 | 5/1975 | Douvas et al. | 606/170 X |
| 3,976,077 | 8/1976 | Kerfoot | 606/170 X |
| 3,990,453 | 11/1976 | Douvas et al. | 606/166 X |
| 4,203,444 | 5/1980 | Bonnell et al. | 606/170 X |
| 4,274,414 | 6/1981 | Johnson et al. | 606/170 |
| 4,306,570 | 12/1981 | Matthews | 128/755 X |
| 4,368,734 | 1/1983 | Banko | 606/170 |
| 4,512,344 | 4/1985 | Barber | 606/170 X |
| 4,649,919 | 3/1987 | Thimsen et al. | 606/170 X |

FOREIGN PATENT DOCUMENTS 2093353 9/1982 United Kingdom ................ 606/170

Primary Examiner—Michael H. Thaler
Attorney, Agent, or Firm—Todd A. Dawson

[57] ABSTRACT

The arthroscopic surgery instrument includes an elongated outer sheath member having substantially fully open distal and proximal ends, and an inner hollow cylindrical cutting blade member rotatable within the sheath member. The cutting blade member has a distal end that is substantially fully open. The cutting blade member and the sheath member are each provided with a pair of spaced longitudinally extending, diametrically opposed tabs at their corresponding distal ends. The spaces between the tabs on the sheath member defines oppositely disposed cutting windows. Cutting edges are formed on each of the tabs on the cutting blade member and the sheath member and extend to the free ends of each member. The cutting edges on the cutting blade member are cooperable with the corresponding cutting edges on the sheath member. A rotary drive motor rotates the cutting blade member relative to the sheath member. Tissue positioned at a selected cutting window during rotation of the cutting blade member can thus be severed as the cutting blade member passes the cutting windows. An aspirator communicates with the interior space of the cutting blade member to remove tissue severed by the cooperable cutting action of the blade and sheath members. The aspiration path is a straight line path through the interior of the cutting blade member.

2 Claims, 5 Drawing Sheets

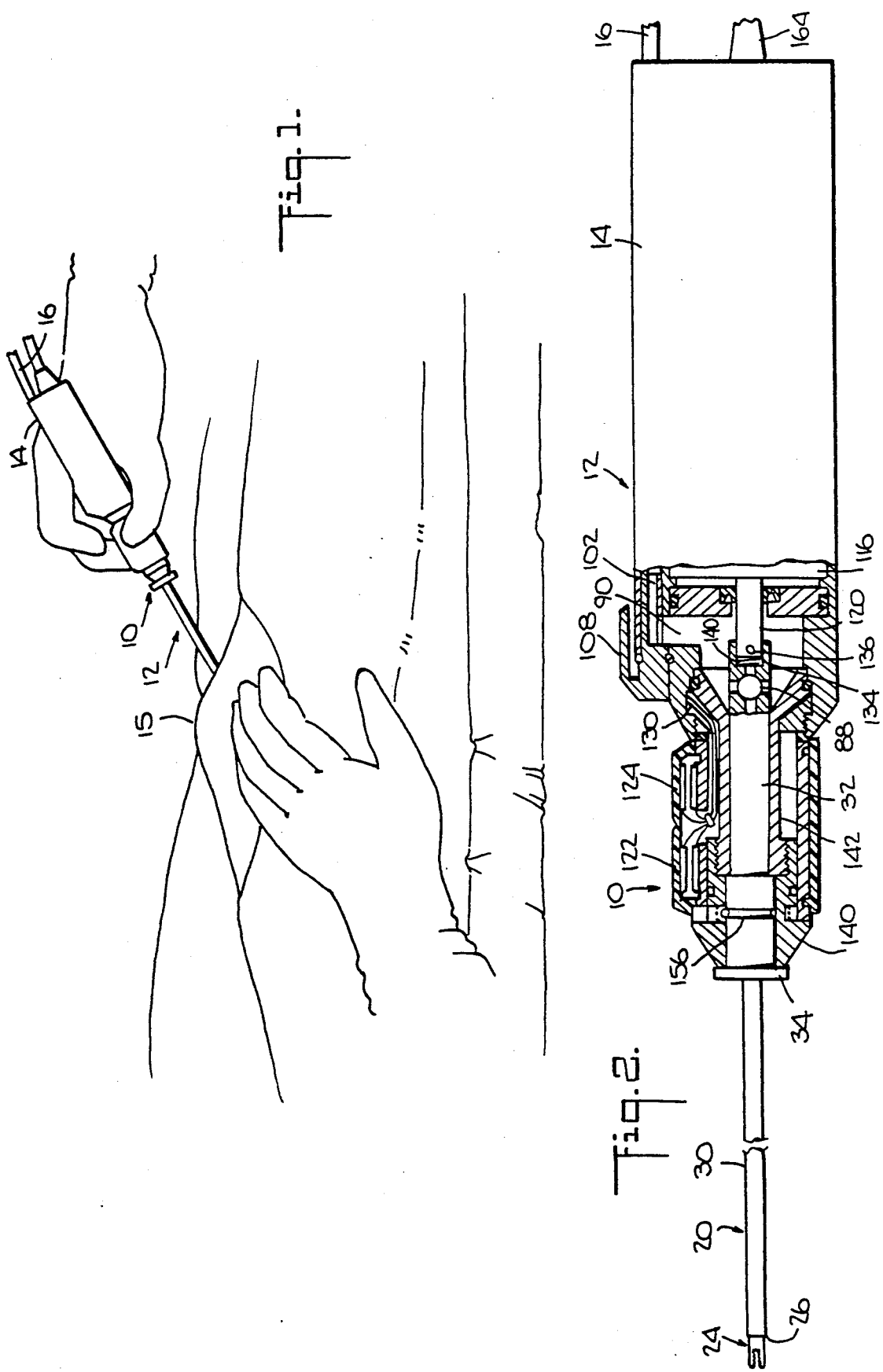

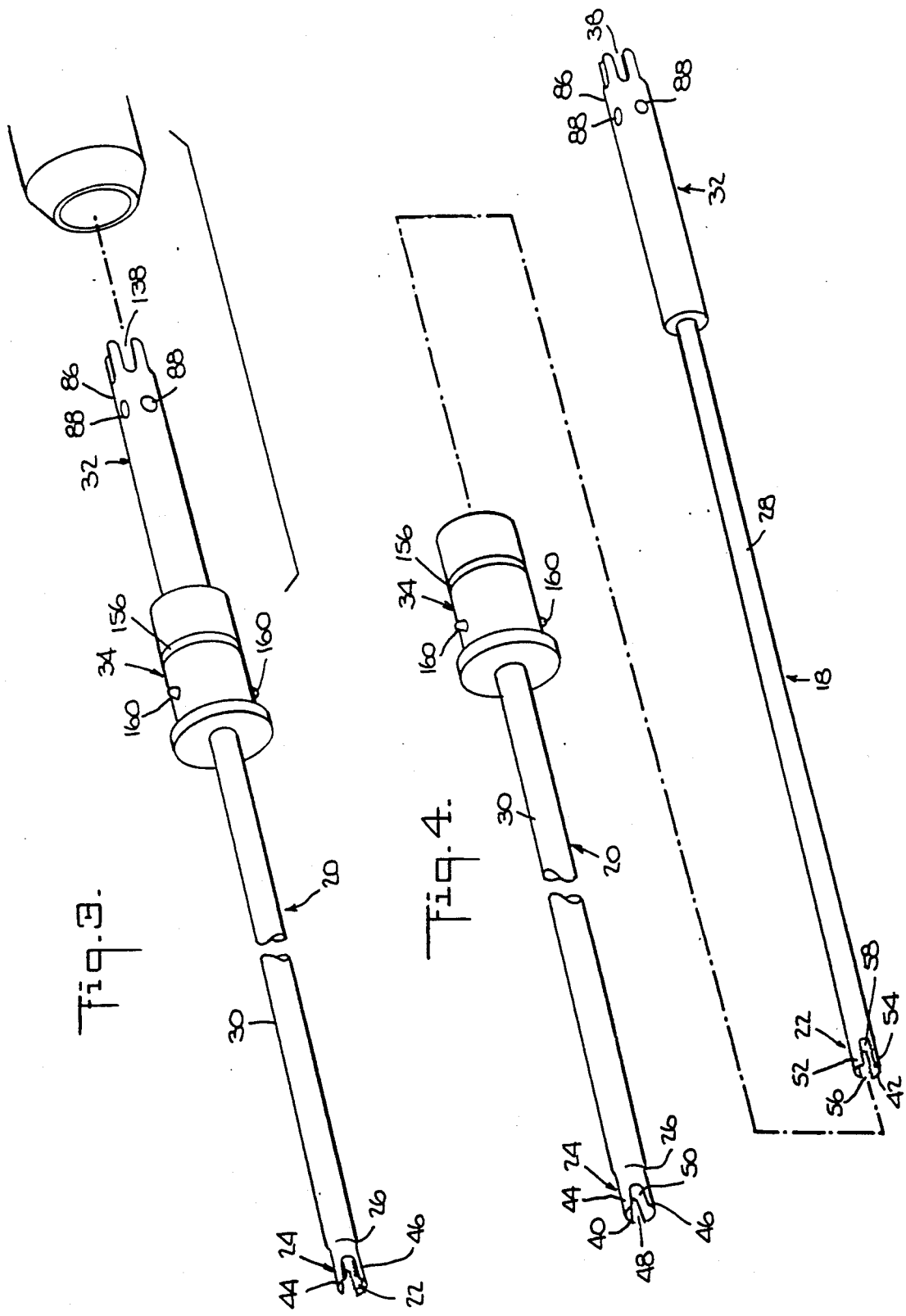

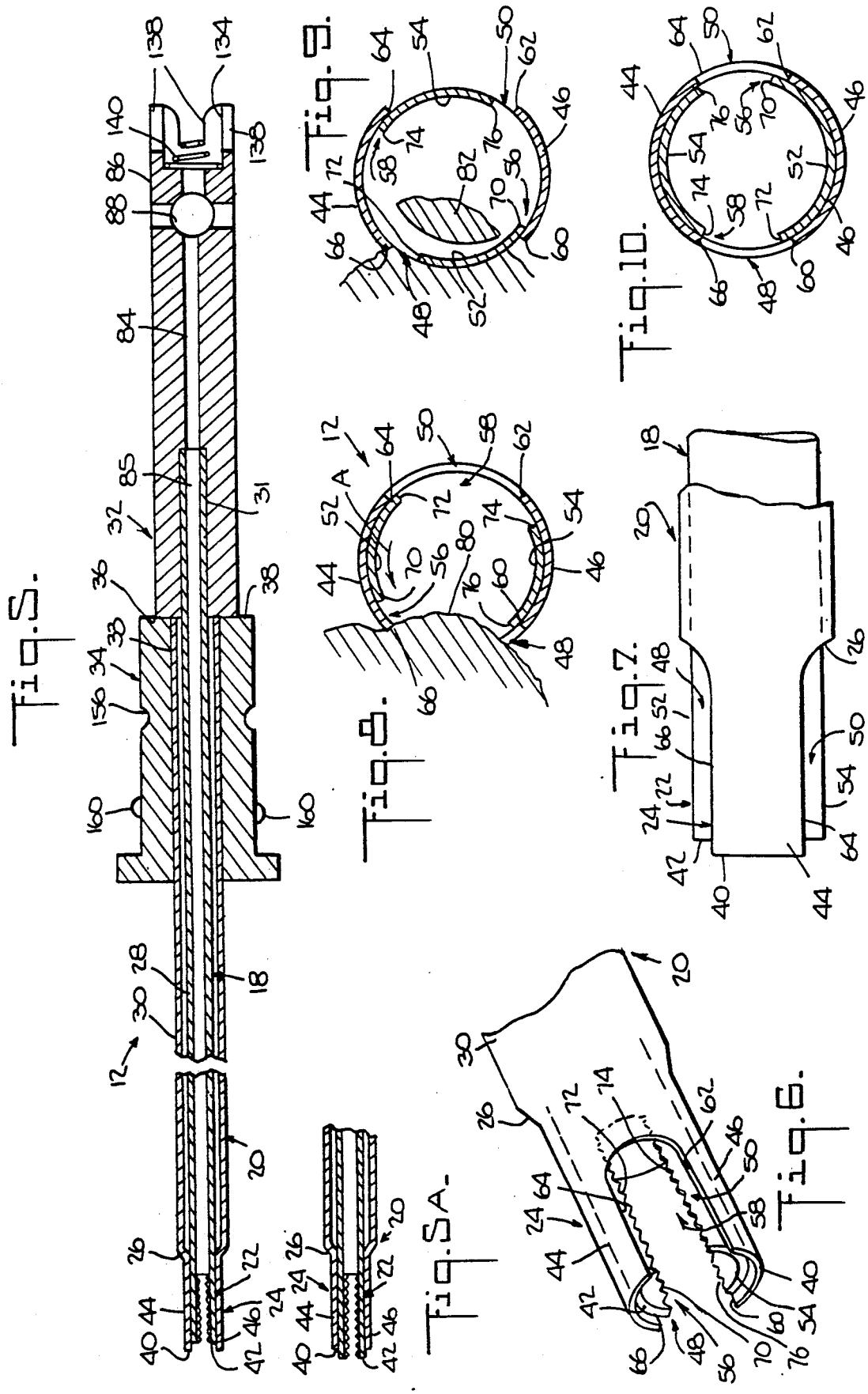

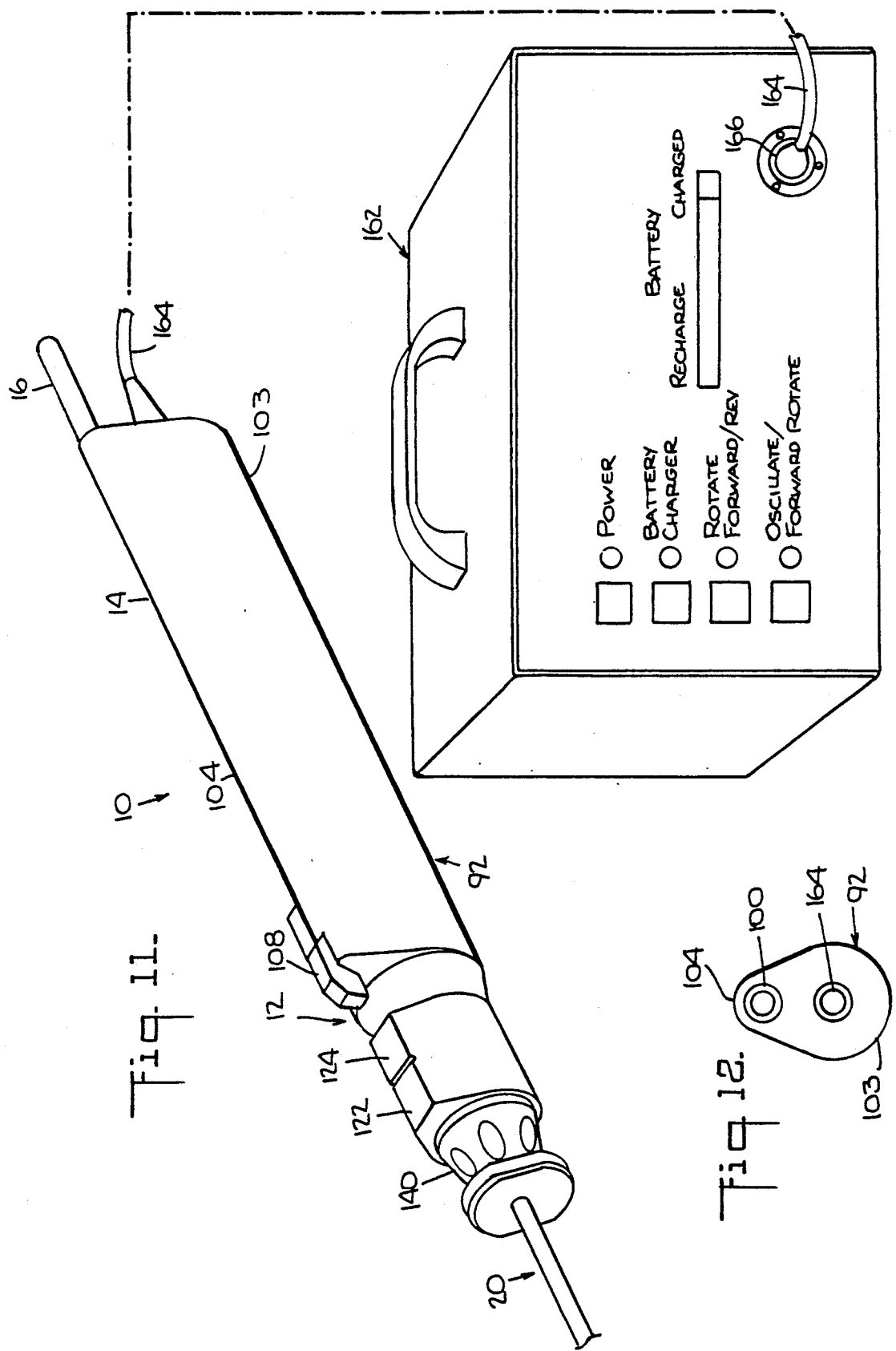

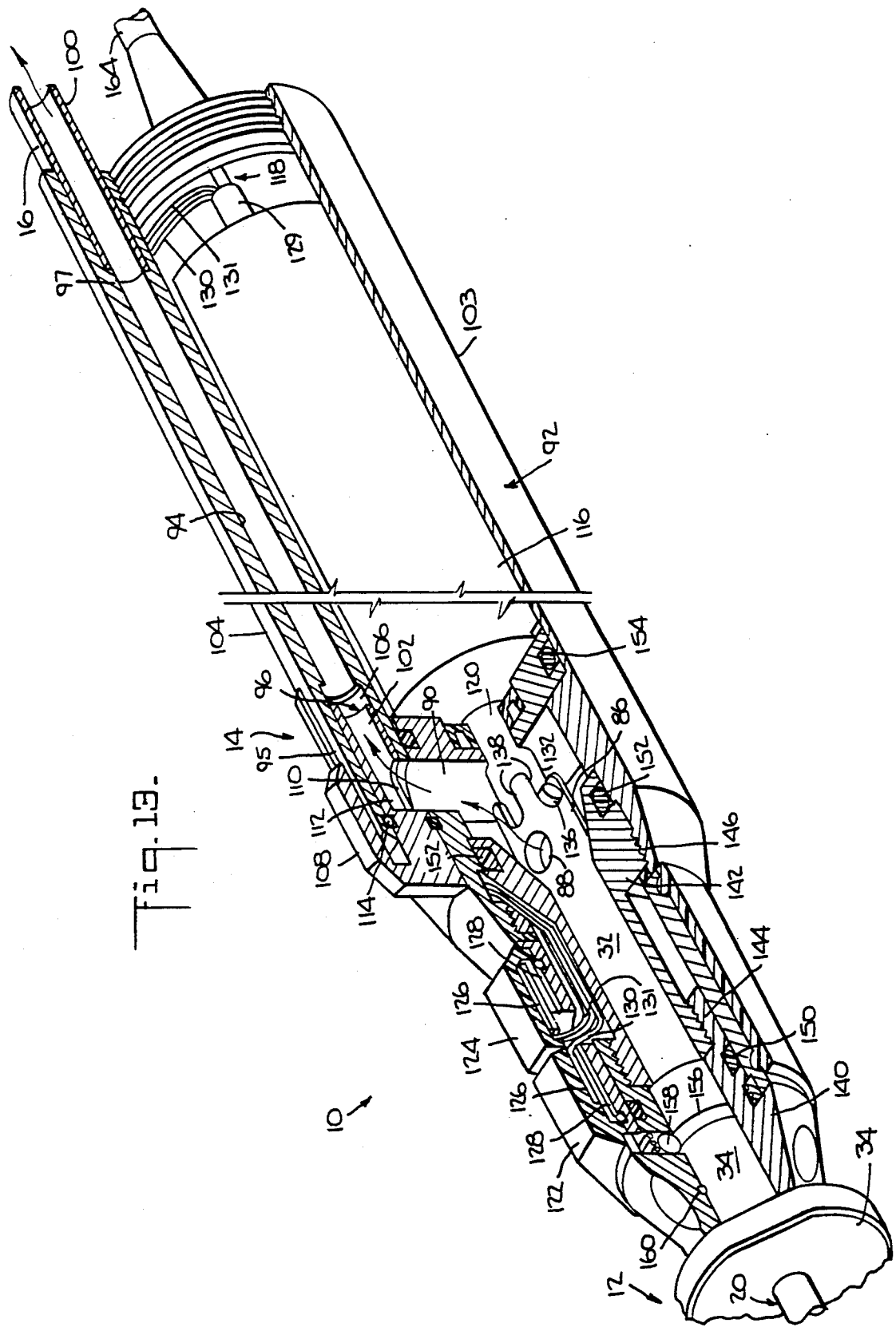

ARTHROSCOPIC SURGICAL APPARATUS AND METHOD

This application is a continuation of application Ser. No. 07/427,438, filed Oct. 25, 1989, now abandoned.

This invention relates to a surgical apparatus and method for cutting tissue and, more particularly to an arthroscopic surgical cutting apparatus that allows a substantially steady flow aspiration of cut tissue while permitting side cutting, end cutting, and reverse cutting, and interchange of different size cutter blades.

In performing arthroscopic surgery, for example, arthroscopic knee surgery or arthroscopic shoulder surgery, it is well known to utilize a cutting device having a stationary outer cylindrical sheath member with an inner rotating cutter blade. The rotating cutter blade cooperates with the sheath member to effect a cutting action at one or more cutting windows formed in the sheath member, usually at a distal end.

Arthroscopic cutter blades are generally in one of two typical forms. One such form, as shown in U.S. Pat. Nos. 4,203,444 and 4,274,414, includes a hollow cylinder having a longitudinal slot at a distal end portion. A side of the slot defines a longitudinally extending cutting edge that coacts with a corresponding cutting edge at a cutting window formed in a surrounding sheath member.

Another typical form of cutter blade, as shown in U.S. Pat. No. 4,649,919, includes a solid helical auger having flutes at a distal end which coact with cutting edges of a sheath window to effect a cutting action.

The cutting edge in arthroscopic cutting devices which employ hollow cylinder cutter blades or solid helical auger cutter blades is usually adapted to entrap the tissue to be cut between the blade cutting edge and sheath window cutting edge. Thus as the rotating motion of the cutter blade produces a shearing action between the cutting edge of the cutting blade and the cutting edge of the sheath window, a portion of tissue is severed each time the blade cutting edge rotates past the sheath cutting edge.

In order to remove the severed tissue from the area of the cutting window, aspiration is often applied to the cutting device, generally at a proximal end of the cutting blade member. The aspirating action is normally effected through the interior of the hollow cylindrical cutter blades or between the interior of the sheath member and the helical flutes, in the auger form of cutter. Aspiration causes the severed material to flow through the hollow cylindrical cutter or through a channel created by the helical flutes of the auger-type cutting blade and the inside diameter of the outer sheath.

In the case of the auger-type cutter blade the aspiration channel is a tortuous path for the severed material to follow and often becomes clogged thus restricting the flow and removal of severed material. Another problem inherent in the auger-type cutters is the increasing prospect for clogging in progressively smaller cutter assemblies since the web of material which interconnects the helical flutes of the auger cutter occupies an increasingly greater proportion of the space used for aspiration as the size of the cutter assembly decreases.

In the case of hollow cylindrical cutter blades, it is common practice to employ outer sheath members in which the distal ends thereof are either fully closed, or substantially fully closed. Thus the aspiration flow passes through the cutting window of the sheath and into the interior of the cutter blade. This arrangement results in a pulsating aspiration flow because the cutting window opens and closes as the cutter blade rotates past the sheath cutting edge. Accordingly, the aspiration flow tends to be intermittent and susceptible to clogging.

A further problem that can arise in current types of arthroscopic cutting apparatus due to the interaction between the cutting edges of the cutting blade and the longitudinal cutting surfaces of the outer sheath, is a pulling and tearing action.

In addition the known arthroscopic cutting devices generally cannot be operated efficiently in both the forward and reverse directions of rotation and throughout the entire speed range of the rotary drive mechanism that drives the cutter. Thus a surgeon using the current types of cutters is normally restricted from approaching damaged tissue at angles other than those that can be used with a single direction cutter.

It is thus desirable to provide an arthroscopic surgical apparatus with improved steady flow aspiration characteristics and capable of side cutting and end cutting as well as efficient operation in forward and reverse directions of rotation.

OBJECTS AND SUMMARY OF THE INVENTION

Among the several objects of the invention may be noted the provision of an arthroscopic cutting apparatus which has an improved aspiration path for the removal of severed material from the area of a cutting window, an arthroscopic cutting apparatus having improved cutting edges on the cutter blade to reduce pulling and tearing, while severing material, an arthroscopic cutting apparatus which can be operated efficiently in both the forward and reverse directions of rotation throughout the entire speed range of the rotary drive mechanism employed therein, an arthroscopic cutting apparatus which permits side cutting and end cutting, an arthroscopic cutting apparatus which includes interchangeable cutter blades of different size, and a novel method of cutting tissue.

Other objects and features of the invention will be in part apparent and in part pointed out hereinafter.

The arthroscopic tissue cutting apparatus in accordance with one embodiment cf the invention, includes a hollow cylindrical sheath member elongated along a longitudinal axis and having substantially fully open distal and proximal ends. A hollow cylindrical blade member is rotatable within the sheath member in closely spaced relationship thereto. The blade member is also elongated along a longitudinal axis and includes distal and proximal ends. The proximal end of the blade member is coupled to an aspirator, and the distal end is substantially fully open.

The sheath member and blade member are each provided with a pair of longitudinally extending, diametrically opposed tabs at their corresponding distal ends. Each of the tabs on the blade and sheath members includes at least one longitudinally extending cutting edge that cooperates with a corresponding cutting edge on the tab of the other member for cutting tissue when the blade member is rotated relative to the sheath member. At least one of the cooperable cutting edges is serrated to minimize pulling or tearing of tissue as it is being severed.

The substantially open ends of the blade member and sheath member, with cutting edges that extend to the respective open ends, permit end cutting as well as side cutting.

A blade member of one selected longitudinal extent is interchangeable with a blade member of another longitudinal extent. Thus one blade member of one longitudinal extent can be recessed in the sheath member, and another blade member of another longitudinal extent can project from the sheath member.

Aspirating means for removing cut material are communicable with the interior of the blade member such that severed tissue is aspirated along a straight line path through the hollow blade member after being cut by the cutting edges on the tabs of the sheath and blade members.

The apparatus is further provided with means including a rotary drive motor coupled to the proximal end of the blade member for rotating the blade member in reverse directions.

The invention accordingly comprises the constructions and methods hereinafter described, the scope of the invention being indicated in the claims.

DESCRIPTION OF THE DRAWINGS

In the accompanying drawings,

FIG. 1 is a simplified diagrammatic view showing an arthroscopic surgical apparatus incorporating one embodiment of the invention being used for surgery of the knee;

FIG. 2 is a side elevation view thereof, partly shown in section;

FIG. 3 is a partially exploded, perspective view thereof showing the cutting portion of the instrument separated from the rotary drive motor and aspirator thereof;

FIG. 4 is a partially exploded, perspective view thereof, similar to FIG. 3, showing the inner cutting blade member separated from the outer cylindrical sheath member;

FIG. 5 is a side elevation view in section of the cutting blade member and the outer sheath member in assembled relationship;

FIG. 5A is a side elevational view in section showing an assembly in which the cutting blade member extends beyond the outer sheath member, FIG. 6 is an enlarged perspective view of the distal end portion thereof;

FIG. 7 is a plan view of the distal end portion thereof with the inner cutting blade rotated approximately 90° relative to the outer sheath member from the position shown in FIG. 6;

FIG. 8 is an enlarged sectional view taken through the distal end portion thereof proximate to a tissue cutting site;

FIG. 9 is a view similar to FIG. 8 after tissue is severed;

FIG. 10 is a view similar to FIG. 9 after the severed tissue has been aspirated;

FIG. 11 is a partial perspective view thereof, showing the rotary drive portion and a portable power pack;

FIG. 12 is an end view thereof; and,

FIG. 13 is an enlarged perspective view thereof showing the rotary drive motor, portions of which are broken away to show interior details.

Corresponding reference characters indicate corresponding parts throughout the several views of the drawings.

DETAILED DESCRIPTION OF THE INVENTION

An arthroscopic surgery instrument incorporating one embodiment of the invention is generally indicated by the reference number 10 in FIG. 1.

The instrument 10 includes an arthroscopic tissue cutting apparatus, shown generally at 12, supported in a rotary drive motor portion, shown generally at 14.

During arthroscopic knee surgery, for example, the arthroscopic tissue cutting apparatus 12 is inserted into a patient's knee joint, below the patella 15 (FIG. 1). At the same time, a fiber-optic device (not shown) introduces light to the interior of the joint and returns a visual image along a separate bundle of fibers, allowing a surgeon to view the procedure. In addition, the knee joint is inflated by introduction of a saline solution into the joint from a source of saline (not shown) under slight hydrostatic pressure.

The saline solution irrigates the knee joint and is continuously aspirated therefrom through the interior of the instrument 10 and an aspiration tube 16.

Referring to FIGS. 2-6, the tissue cutting apparatus 12 includes a hollow cylindrical cutting blade member 18 which is telescopically and rotatably mounted within a stationary outer cylindrical sheath member 20. As best shown in FIG. 5, a distal end portion 22 of the cutting blade member 18 is rotatably journaled in a distal end portion 24 of the outer cylindrical sheath member 20.

Preferably, the outer diameter of the distal end portion 22 of the cutting blade member 18 is approximately 0.0002 inches to 0.0005 inches smaller than the inner diameter of the distal end portion 24 of the sheath member 20 to enable the distal end portion 24 of the sheath member 20 to serve as a suitable bearing support for the distal end portion 22 of the cutting blade member 18.

The outer sheath member 20 is provided with a shoulder or step 26, at which the inner diameter of the sheath member 20 is enlarged relative to the outer diameter of the blade member 18. Thus a greater clearance in the range of 0.002 inches to 0.005 inches is provided between a non-distal portion 30 of the sheath member 20 and a non-distal portion 28 of the blade member 18 than that which is provided at the distal end portions 22 and 24 thereof.

A proximal end portion 31 of the cutting blade member 18 is carried by and fixed to the interior of a collar member 32. Similarly, a proximal end portion 33 of the outer sheath member 20 is carried by and fixed to the interior of a collar member 34. When the cutting blade member 18, as held by the collar member 32, is fully telescoped into the interior of the sheath member 20, as held by the collar member 34, an end surface 36 (FIG. 5) on the collar member 32 abuts against an end surface 38 on the collar member 34. Under this arrangement, a free end 40 of the sheath member 20 extends a predetermined amount such as 0.030 inches for example, longitudinally beyond a free end 42 of the cutting blade member 18 to shield the end of the cutting blade member 18 during the performance of arthroscopic surgery.

If desired, the recessed cutting blade member 18 can be replaced by one that is slightly longer so that the free distal ends 40 and 42 of both the cutting blade member 18 and the sheath member 20 are positioned flush with one another to enhance the ability of the arthroscopic tissue cutting apparatus 12 to provide end-wise cutting or boring of tissue. Also, if desired, the free distal end 42 of the cutting blade member 18 can extend longitudinally beyond the free distal end 40 of the sheath member 20 for selected surgical procedures (FIG. 5A). The cutting blade 18 can thus be interchanged with other cutting blades 18 of the same or slightly different longitudinal extents. Alternatively, the sheath member 20 can be replaced with another sheath member of different extent to achieve a desired relative relationship between the free distal ends 40 and 42.

Referring to FIGS. 6 and 7, the distal end portion 24 of the sheath member 20 includes a pair of longitudinally extending, diametrically opposed tabs 44 and 46. The tabs 44 and 46 are each of approximately 90° circumferential extent, for example, and are spaced by open areas or cutting windows 48 and 50 having approximately 90° circumferential extent, for example. Similarly, the distal end portion 22 of the blade member 18 is provided with a pair of longitudinally extending, diametrically opposed tabs 52 and 54 which are each of approximately 90° circumferential extent, for example, and are spaced apart from one another by open areas, or cutting windows 56 and 58. It should be noted that the circumferential extents of the tabs 44, 46, 52, 54 and the cutting windows 56 and 58 can differ from the foregoing example in accordance with specific surgical requirements.

The distal tabs 44 and 46 of the sheath member 20 are provided with cutting edges 60, 62, 64 and 66 (FIGS. 6 and 10) that are straight and parallel to the longitudinal axis of the sheath member 20. The cutting edges 60, 62, 64 and 66 are formed with sharpened radially inner edges. The distal tabs 52 and 54 of the cutting blade member 18 are provided with serrated, sharpened cutting edges 70, 72, 74 and 76. The tips of the serrations forming the respective cutting edges 70, 72, 74 and 76 are preferably aligned in a line that is parallel to the longitudinal axis of the cutting blade member 18.

When the cutting blade member 18 rotates within the sheath member 20, either in one direction of rotation or another, the serrated edges 70, 72, 74 and 76 of the tabs 52 and 54 on the cutting blade member 18 effect a cutting action in cooperation with the straight cutting edges 60, 62, 64 and 66 on the tabs 44 and 46 of the sheath member 20 to sever any portions of tissue positioned within one or the other of the windows 48 and 50.

Referring to FIGS. 5 and 8, tissue such as shown generally at 80, is introduced into the cutting window 48 of the tissue cutting apparatus 12. The tab 52 of the cutting blade member 18 rotates into the window area 48 of the sheath member, in the direction of the arrow A, for example. The serrated edge 70 thus engages the projecting tissue material 80, entrapping the material on one or more of the serration tips and cutting it against the sharpened edge 60 of the tab 46 thereby severing a portion of tissue, as indicated at 82 in FIG. 9.

The serrated tooth arrangement greatly reduces the pulling and tearing that can often occur with current auger cutters and non-serrated cutters. As the tab 52 completes its rotation past the window 48, the severed tissue 82 is aspirated and removed from the window area such that the blade member 18 is prepared for further severing action as indicated in FIG. 10.

Referring to FIGS. 5 and 13, the collar member 32 is a generally hollow structure that includes a central longitudinal passageway 84 that communicates with the hollow interior 85 of the blade member 18. The collar member 32 also includes radially oriented apertures 88 adjacent a proximal end 86. The apertures 88 connect the passageway 84 with a chamber 90 (FIG. 13) formed in the interior of the rotary drive motor portion 14 of the instrument 10.

Referring to FIGS. 11 and 12, the rotary drive motor portion 14 of the instrument 10 includes a rear outer casing 92 having a lower portion 103 of generally circular cross-sectional configuration, and an upper portion 104 of generally triangular cross-sectional configuration.

Referring to FIG. 13, an interior conduit 94 provided in the upper portion 104 has an upstream end portion 95 that communicates with the chamber 90 through a cut-off valve mechanism 96. A downstream end portion 97 of the conduit 94 communicates with the aspiration tube 16, which provides a sub-atmospheric pressure or suction to the interior space 85 of the cutting blade member 18 for removing severed tissue therefrom.

The aspiration tube 16 is adapted to be connected to a conventional source of sub-atmospheric pressure or suction (not shown).

The cut-off valve mechanism 96 includes a rotary valve member 102 that is rotatable relative to the upper portion 104 of the housing 92 within a cylindrical passageway 106 formed in the upper portion 104. The valve member 102 is connected to an external actuating arm 108 which may be rotated relative to the chamber 106 to cause an opening 110 in the valve member 102 to be moved into or out of alignment with the chamber 90.

When the valve member opening 110 is in alignment with the chamber 90, suction from the aspiration tube 16 can be applied to the chamber 90, and to the interior space 85 of cutting blade member 18. When the valve member opening 110 is rotated out of alignment with the chamber 90, a blank portion 112 of the valve member 102 is disposed between the aspiration tube 16 and the chamber 90 to prevent suction from reaching the interior space 85 of the cutting blade member 18.

The valve member 102 is provided with a suitable sealing "O" ring 114 to prevent atmospheric air from entering the suction chamber 90 and the suction conduit 94 of the instrument 10.

The rear outer casing 92 encloses a conventional drive motor 116. The drive motor 116 includes an output shaft 120 that can be rotated in a forward or reverse direction, depending upon which of two control switches, 122 and 124, are depressed.

The control switches 122 and 124 (FIG. 13) each include upper and lower contacts 126 and 128, respectively, that are connected by cables 130 and 131 to a multi-conductor instrument cable 129 at a splice juncture 118. The switches 122 and 124 control the direction of rotation of the motor shaft 120 in a known manner. Preferably, the upper contacts 126 of the switches 122 and 124 are embedded in a silicone rubber matrix that can be easily depressed by the user of the instrument 10.

A forward end portion 132 of the motor output shaft 120 fits snugly within an opening 134 (FIG. 5) formed in the proximal end portion 86 of the collar 32. The motor shaft end portion 132 also carries a transversely oriented pin 136, the outer end portions of which fit within and drivingly engage longitudinal slots 138 formed in the proximal end portion 86 of the collar 32. A spring 140 (FIG. 5) is provided in the opening 134 to axially bias the collar 32 into engagement with the collar 34 when the motor shaft end portion 132 engages the collar opening 134. Under this arrangement, the shaft 120 also serves as a rear support and centering device for the cutting blade member 18.

The rotary drive motor portion 14 further includes a forward casing portion 140 and an intermediate casing portion 142. The forward casing portion 140 is detachably connected to the intermediate casing portion 142 by threads 144, and the intermediate casing portion 142 is detachably connected to the rear casing portion 92 at threads 146. Thus the forward and intermediate casing portions 140 and 142 may be separated from one another and from the rear casing 92 to allow access to the interior of the drive motor portion 14 and the rear casing 92.

Axially spaced elastomeric sealing rings 150, 152 and 154 are provided at the forward casing portion 140, the intermediate casing portion 142 and the rear casing portion 92. The sealing rings 150, 152 and 154 help prevent introduction of atmospheric air into the interior of the rotary drive motor portion of the instrument 10, to ensure leak-tight aspiration from the interior space 85 of the cutting blade member 18.

A detent groove 156 is provided in the collar 34 of outer sheath member 20 to longitudinally align the collar 34 with the forward casing portion 140. A detent ball 158 is biased into the groove 156 to retain the collar 34 in a predetermined longitudinal position relative to the forward casing 140. In addition, a pair of detent pin members 160 (FIGS. 3, 4 and 13) are biased radially outwardly from the collar 34 into engagement with corresponding openings in the interior of the forward casing 140 to prevent the collar 34 and the stationary outer sheath 20 from rotating relative to the forward casing 140.

Referring to FIGS. 11 and 13, the rotary drive motor 116 is powered by a portable power pack 162, having batteries (not shown) that are rechargable by a conventional recharging circuit (not shown). The power pack 162 is connected to the instrument 10 via a cable 164 and a connector 166. The instrument 10 is thus portable and convenient to use.

Some advantages of the invention evident from the foregoing description include an arthroscopic cutting apparatus that permits both side trimming and end trimming with the same cutting blade. A surgeon thus has a greater degree of flexibility in which to perform a surgical procedure. The end cutting ability of the arthroscopic cutting apparatus allows the cutter to act as a coring device when tissue or material is approached perpendicular to the normal cutting axis. An interchangeable blade feature adds further versatility to the apparatus.

The open end of the cutting apparatus and the hollow space within the cutting blade allows a short, direct and relatively wide fluid flow path for the aspiration media which in turn increases the ability of the apparatus to remove particulate material from the surgical site. Thus miniaturization of the apparatus is feasible without adversely affecting the aspiration ability of the miniaturized device.

A further advantage is the provision of improved cutting edges on the cutter blade member to reduce the pulling and tearing that can occur with previously used cutter arrangements. The arthroscopic cutting apparatus is efficiently operable in both forward and reverse directions of rotation throughout the entire speed range of the rotary drive mechanism. Thus a surgeon can approach tissue at angles that could not be used with a single direction cutter.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An arthroscopic tissue cutting apparatus adapted to be coupled to an aspirator and to a rotary drive motor, said apparatus comprising a hollow, cylindrical sheath member elongated along a longitudinal axis and having a substantially fully open distal end, and a hollow cylindrical blade member rotatable within said sheath member, said blade member being elongated along an axis corresponding to said longitudinal axis and having an open interior space, said blade member having a proximal end adapted to be coupled to said aspirator, and a substantially fully open distal end, the distal end of said blade member extending a predetermined longitudinal amount beyond the distal end of said sheath member, the respective distal ends of said blade member and said sheath member each being provided with a pair of spaced, longitudinally extending, diametrically opposed tabs, each of said tabs on each of said blade and sheath members including at least one longitudinally extending cutting edge, the cutting edges on the tabs of one of said blade and sheath members being cooperable with the corresponding cutting edges on the tabs of the other of said blade and sheath members for cutting tissue positioned in the space between the tabs of said sheath member when said blade member is rotated relative to said sheath member, said cut tissue being aspirated through the interior space of said hollow blade member.

2. A method of cutting tissue comprising
   (a) locating a generally tubular inner blade member with an interior space within an outer tubular sheath member with an interior space within an outer tubular sheath member to permit rotation of the inner blade member with respect to the outer sheath member,
   (b) arranging a distal end portion of the inner blade member with a pair of spaced opposing tabs that extend to a free end of the inner blade member,
   (c) forming at least one cutting edge on each of the inner blade member tabs that extends to the free end of the inner blade member,
   (d) arranging a distal end portion of the outer sheath member with a pair of spaced opposing tabs that extend to a free end of the sheath member,
   (e) forming at least one cutting edge on each of the outer sheath member tabs that extends to the free end of the outer sheath member,
   (f) positioning the inner blade member with respect to the outer sheath member such that the sheath tabs can overlap the blade tabs and the free end of the inner blade member is recessed with respect to the free end of the outer sheath member,
   (g) rotating the inner blade member with respect to the outer sheath member such that the cutting edges on the inner blade member tabs and the cutting edges on the outer sheath member tabs cooperate to form a cutting action to cut tissue,
   (h) aspirating the cut tissue through the interior space of the inner blade member, and
   (i) interchanging the inner blade member with another inner blade member of different length such that the free end of the other inner blade member projects beyond the free end of the outer sheath member.

* * * * *